US008435195B2

(12) United States Patent
Kudoh et al.

(10) Patent No.: US 8,435,195 B2
(45) Date of Patent: *May 7, 2013

(54) WALKING ASSISTANCE DEVICE

(75) Inventors: Hiroshi Kudoh, Wako (JP); Yosuke Endo, Wako (JP); Yasushi Ikeuchi, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 688 days.

This patent is subject to a terminal disclaimer.

(21) Appl. No.: 12/667,479

(22) PCT Filed: May 16, 2008

(86) PCT No.: PCT/JP2008/001233
§ 371 (c)(1),
(2), (4) Date: Dec. 31, 2009

(87) PCT Pub. No.: WO2009/004754
PCT Pub. Date: Jan. 8, 2009

(65) Prior Publication Data
US 2010/0145239 A1 Jun. 10, 2010

(30) Foreign Application Priority Data
Jul. 2, 2007 (JP) ................................. 2007-173953

(51) Int. Cl.
*A61F 5/00* (2006.01)
(52) U.S. Cl.
USPC ............................................ 602/16; 602/19

(58) Field of Classification Search .................. 602/4, 5, 602/16, 19; 128/869; 482/51, 66
See application file for complete search history.

(56) References Cited

U.S. PATENT DOCUMENTS
7,731,674 B2 * 6/2010 Ashihara et al. ................ 602/16

FOREIGN PATENT DOCUMENTS
| JP | 2003-210537 | 7/2003 |
| JP | 2006-204426 | 8/2006 |
| JP | 2006-204730 | 8/2006 |
| JP | 2007-020909 | 2/2007 |

* cited by examiner

*Primary Examiner* — Nicholas Lucchesi
*Assistant Examiner* — Pritesh Patel
(74) *Attorney, Agent, or Firm* — Rankin, Hill & Clark LLP

(57) ABSTRACT

A walking assistance device has a load transmitting assembly, a foot-worn assembly, and a leg link provided between the load transmitting assembly and the foot-worn assembly. The foot-worn assembly has a ground contact member, on which a user's foot rests, and a connecting member which connects the ground contact member to a joint at a lower end of the leg link. The ground contact member is provided with tread force sensors and the foot-worn assembly permits detection of a tread force. The connecting member is formed so as to rise in a cantilever manner from one lateral side of the ground contact member. The tread force sensors are installed in at least one location adjacent to the heel of the user's foot and in at least two locations adjacent to toes of the user's foot, with the latter two locations being laterally spaced apart.

3 Claims, 3 Drawing Sheets

WALKING ASSISTANCE DEVICE

TECHNICAL FIELD

The present invention relates to a walking assistance device which reduces load acting on a leg or legs of a user thereby to assist walking of the user.

BACKGROUND ART

Hitherto, as this type of walking assistance device, there has been known one having a load transmitting assembly, a foot-worn assembly to be attached to a foot of a user, and a leg link provided between the load transmitting assembly and the foot-worn assembly (refer to, for example, Japanese Patent Application Laid-Open No. 2007-20909). According to this device, at least a part of the weight of a user is supported by the leg link through the intermediary of the load transmitting assembly to reduce load acting on a leg of the user, thereby assisting the walking.

In the conventional example described above, the foot-worn assembly includes a shoe having a sole, which is a ground contact member on which a foot of the user is rested, and a connecting member, which connects the shoe to a joint provided at a lower end of the leg link. The connecting member is formed like a stirrup, into which a toe portion of the user can be inserted, and is attached to the shoe.

Further, in the conventional example described above, tread force sensors are provided on the sole, in one location adjacent to the heel of a foot of the user and in another location adjacent to a toe (at the proximal end of a big toe), to detect a tread force of the user. Further, the support force provided by the leg link is variably controlled according to the tread force of a leg of the user detected by the tread force sensors.

In the stirrup-shaped connecting member of the aforesaid conventional example, a foot of the user is inserted into the connecting member, so that the freedom of the motion of the foot will be limited, thus inconveniently making the user feel restrained. Hence, it is desired to secure the freedom of foot motions so as to provide more comfortable fit of the foot-worn assembly.

However, merely securing the freedom of foot motions presents the following problem. An influence of a habitual walking pattern of each user will prominently manifest, occasionally resulting in a major load being applied to the outer side in the lateral direction of a foot or a major load being applied to the inner side in the lateral direction thereof. Thus, the tread force sensors provided in only a total of two locations, one adjacent to the heel of a foot and the other adjacent to the toe, as in the aforesaid conventional example, fail to accurately detect the tread forces of the user.

DISCLOSURE OF INVENTION

Problem to be Solved by the Invention

The present invention has been made in view of the background described above, and it is an object thereof to provide a walking assistance device which assures more comfortable fit of a foot-worn assembly and which also permits accurate detection of tread forces of a user.

Means to Solve the Problem

To fulfill the object described above, the present invention provides a walking assistance device comprising a load transmitting assembly, a foot-worn assembly to be attached to a foot of a user, and a leg link provided between the load transmitting assembly and the foot-worn assembly, wherein at least a part of the weight of the user is supported by the leg link through the intermediary of the load transmitting assembly, the foot-worn assembly includes a ground contact member on which a foot of the user is rested and a connecting member which connects the ground contact member to a joint provided at a lower end of the leg link, the ground contact member is provided with tread force sensors for detecting a tread force of the user, the connecting member is formed so as to rise in a cantilever manner from one lateral side of the ground contact member, and the tread force sensors are installed in at least one location adjacent to the heel of a foot of the user and in at least two locations adjacent to a toe, the two locations being laterally spaced away from each other.

According to the present invention, the connecting member rises in the cantilever manner from one lateral side of the ground contact member, so that a foot of a user is not restrained by the connecting member. As a result, the freedom of foot motions is secured, leading to more comfortable fit of the foot-worn assembly.

Further, since the freedom of foot motions is secured, the tread force of the user can be accurately detected even if major load is applied to the laterally outer side of a foot or if major load is applied to the laterally inner side thereof. In other words, according to the present invention, the tread force sensors are installed in at least two locations adjacent to the toe, the two locations being laterally spaced apart from each other. Therefore, in the case where major load is applied to the laterally outer side of a foot, the tread force of the user can be accurately detected by the tread force sensor positioned adjacently to the toe side and to the laterally outer side and the tread force sensor adjacent to the heel. Further, in the case where major load is applied to the laterally inner side of the foot, the tread force of the user can be accurately detected by the tread force sensor positioned adjacently to the toe and to the laterally inner side and the tread force sensor adjacent to the heel.

Further, in the present invention, the tread force sensor is preferably constituted of a base plate, a load detector which is provided on the base plate to detect load, an elastic member covering the load detector, and an upper plate composed of a rigid plate rested on the elastic member. Here, the direction in which a tread force acts changes while walking. Since the tread force sensors are constructed as described above, even if a tread force is input to the upper plate from a direction inclined relative to a vertical direction of the load detector, the tread force is efficiently transmitted to the load detector from the vertical direction due to an internal stress of the elastic member. Accordingly, the sensitivity to tread forces in directions besides the vertical direction is improved, thus allowing tread force detection failure to be reduced.

Providing a tread plate member, which is connected to the lower end of the connecting member and which is to be stepped on by a foot of the user, on the ground contact member makes it possible to prevent the connecting member from wobbling due to a force transmitted from a leg link. In this case, the tread force sensors are preferably installed such that the upper plate does not interfere with the tread plate member. This arrangement prevents the force which is transmitted to the tread plate member from the leg link through the connecting member from being input to the tread force sensors. Hence, the tread forces of the user can be accurately detected without being influenced by the forces generated at the leg link.

BEST MODE FOR CARRYING OUT THE INVENTION

The following will describe a walking assistance device according to an embodiment of the present invention. As illustrated in FIG. 1 and FIG. 2, the walking assistance device has a seating member 1 serving as a load transmitting assembly on which a user P sits astride, a pair of right and left foot-worn assemblies 2 and 2 to be attached to the right and left feet of the user, and a pair of right and left leg links 3 and 3 provided between the seating member 1 and the right and left foot-worn assemblies 2 and 2.

Each of the leg links 3 is formed of a bendable link constituted of a first link member 32, which is connected to the seating member 1 through a first joint 31 at an upper end such that the first link member 32 is longitudinally swingable, and a second link member 34, which is connected to a lower end of the first link member 32 through a rotary second joint 33. The foot-worn assembly 2 is connected to a lower end of the second link member 34 through a third joint 35.

Further, a drive unit 4 for the second joint 33 is mounted on the first link member 32. The second joint 33 is rotationally driven by the drive unit 4 to actuate each of the leg links 3 in a stretching direction, that is, in the direction in which the seating member 1 is pushed up, thereby generating a support force for supporting at least a part of the weight of the user (hereinafter referred to as "the body weight support assisting force"). The body weight support assisting force generated in the leg link 3 is transferred to the body trunk of the user P through the intermediary of the seating assembly 1, thus reducing the load acting on the leg or legs of the user P.

The seating assembly 1 is composed of a saddle-shaped seat 1a, on which the user P sits, and a support frame 1b on a lower surface supporting the seat 1a.

The first joint 31 at the upper end of each of the leg links 3 has an arcuate guide rail 31a provided at the lower side of the seating member 1. Each of the leg links 3 is movably engaged with the guide rail 31a through the intermediary of a plurality of rollers 32b rotatably attached to a slider 32a fixed on the upper end of the first link member 32. Thus, each of the leg links 3 swings in the longitudinal direction about the center of the curvature of the guide rail 31a. The supporting point of the swing of each of the leg links 3 in the longitudinal direction provides the center of the curvature of the guide rail 31a.

Further, the guide rail 31a is rotatably supported by a front end rising portion of the support frame 1b of the seating member 1 through the intermediary of a support shaft 31b, which is long in the longitudinal direction. Hence, the guide rail 31a is connected to the seating member 1 such that the guide rail 31a may swing in the lateral direction. This allows each of the leg links 3 to swing in the lateral direction, enabling a leg of the user P to abduct. The curvature center of the guide rail 31a and the axial line of the support shaft 31b are positioned above the seat 1a. This makes it possible to prevent the seating member 1 from significantly tilting vertically or laterally when the weight of the user P shifts.

The drive unit 4 is constituted of an electric motor 41, a speed reducer 42 connected thereto, and a transmission link 43 connecting a crank arm 42a, which is an output member of the speed reducer 42, and the upper end of the second link member 34 extending upward beyond a joint shaft 33a of the second joint 33. With this arrangement, the motive power output from the electric motor 41 through the intermediary of the speed reducer 42 is transferred to the second link member 34 through the intermediary of the transmission link 43. Then, the second link member 34 swings about the joint shaft 33a relative to the first link member 32, causing the leg link 3 to bend or stretch.

Each of the foot-worn assemblies 2 includes a shoe 21 having a sole 21a serving as a ground contact member, and a connecting member 22 built in the shoe 21. Further, the connecting member 22 is connected to the third joint 35 at the lower end of each of the leg links 3 at a position in front of an ankle of the user P. The third joint 35 has three shafts, namely, a first shaft 35a extending in the lateral direction, a second shaft 35b extending in the vertical direction, and a third shaft 35c extending in the longitudinal direction, as viewed from the front. The position of the third joint 35 is set such that the downwardly extended line of the line connecting the third shaft 35c and the support shaft 31b of the first joint 31 passes in the lateral width of the sole 21a. This arrangement protects the shoe 21 from being subjected to a moment which overturns the shoe 21 due to a body weight support assisting force acting on the connecting line.

Referring to FIG. 3, the shoe 21 has tread force sensors 5, which will be described in detail later, positioned on the sole 21a. Further, an insole 21b is provided in the shoe 21, covering the tread force sensors 5 from above. Further, the third joint 35 has a two-axis force sensor 6 built therein. Detection signals of these tread force sensors 5 and the force sensor 6 are input to a controller 7 accommodated in the support frame 1b of the seating assembly 1. Based on signals from the tread force sensors 5 and the force sensor 6, the controller 7 controls the electric motor 41 to drive the second joint 33 of the leg link 3, thus carrying out walking assistance control for generating the aforesaid body weight support assisting force.

Here, in a sagittal plane (a vertical projection plane along the longitudinal direction), the body weight support assisting force acts on the line connecting the longitudinal swing support point of the leg link 3 in the first joint 31 and the first shaft 35a serving as the longitudinal swing support point of the leg link 3 in the third joint 35 (hereinafter referred to as "the reference line"). Accordingly, in the walking assistance control, the actual body weight support assisting force acting on the reference line (precisely, the resultant force of the body weight support assisting force and the force from the weights of the seating member 1 and each of the leg links 3) is calculated on the basis of the detection values of the forces in the directions of two axes detected by the force sensor 6. Further, the ratio of the tread force of each foot in relation to a total tread force applied to both feet of the user P is calculated on the basis of the forces detected by the tread force sensors 5 of each of the foot-worn assemblies 2. Subsequently, a value obtained by multiplying a set value of a body weight support assisting force, which is set beforehand, by the ratio of the tread force of each foot is calculated as a control target value of the body weight assisting force to be generated at each of the leg links 3. Then, the electric motor 41 is controlled such that the actual body weight support assisting force calculated on the basis of the detection values of the force sensor 6 agrees with the control target value.

Meanwhile, the connecting member 22 of the foot-worn assembly 2 is connected so as to have the freedom of rotation about an axial line in the lateral direction, as observed from the front, relative to the leg link 3, that is, about the first shaft 35a of the third joint 35. Hence, the direction in which the load (body weight support assisting force) transmitted to the connecting member 22 from the leg link 3 is applied tilts forward and backward while walking, so that a rotational moment in the longitudinal direction acts on the connecting member 22. The longitudinal wobbling of the connecting member 22 due to the rotational moment causes wear damage to a portion of the shoe 21 that is in contact with the connecting member 22, thus impairing the durability of the shoe 21.

Therefore, according to the present embodiment, as illustrated in FIGS. 3(a) and 3(b), a tread plate member 23 formed of a rigid plate, which can be stepped on by a foot F of the user at outside the acting range in the sagittal plane of load transmitted from the leg link 3 to the connecting member 22, is provided, and the tread plate member 23 is laid between the insole 21b and the sole 21a. Further, the connecting member 22 is coupled to the tread plate member 23 such that the rotation about the axial line in the lateral direction, as observed from the front, relative to the tread plate member 23 is restricted. Incidentally, FIG. 3(a) omits portions except the sole 21a and the insole 21b of the shoe 21, and FIG. 3(b) omits also the insole 21b. In FIG. 3(a), reference numeral 22a denotes a mounting hole for the first shaft 35a of the third joint 35, the mounting hole being formed in the connecting member 22.

Here, the heel of the foot F is positioned behind the acting range in a sagittal plane of the load transmitted to the connecting member 22 from the leg link 3. Hence, according to the present embodiment, the tread plate member 23 can be stepped on by the heel. Further, the tread plate member 23 and the connecting member 22 are formed into one piece.

According to the construction described above, even if a longitudinal rotational moment acts on the connecting member 22, the tread plate member 23 is stepped on by a heel of the user at outside the load acting range, thus preventing the longitudinal wobbling of the connecting member 22 coupled to the tread plate member 23. Thus, the wear damage to the shoe 21 due to the wobbling of the connecting member 22 does not occur, leading to improved durability of the foot-worn assembly 2.

In addition, the stability of the connecting member 22 is secured by stepping on the tread plate member 23, as described above, thus obviating the need for fixing the connecting member 22 to the shoe 21 by bonding or the like. Hence, the tread plate member 23 to which the connecting member 22 has been joined has simply to be inserted into the shoe 21. This arrangement obviates the need for fabricating a dedicated shoe with a fixed connecting member 22, leading to greater convenience.

Further, in the present embodiment, the connecting member 22 is formed to rise in the cantilever manner from one lateral side of the sole 21a. To describe in more detail, the connecting member 22 is connected to the tread plate member 23 in the cantilever manner such that the connecting member 22 rises from the tread plate member 23 at laterally inner side of a portion between an MP joint Fa and a navicular bone Fb of the foot F of the user. According to this, unlike the stirrup-shaped connecting member in the aforesaid conventional example, the foot F is not restrained by the connecting member 22 and the motional freedom of the foot F is secured, leading to more comfortable fit of the foot-worn assembly 2.

The tread plate member 23 has a portion which extends toward the front from the portion stepped on by the heel of the foot F, and the front portion ends before the MP joint Fa of the foot F. In this arrangement, the tread plate member 23 may be displaced toward the front in the shoe 21. Therefore, the tread plate member 23 is provided with an extension plate 23a, which reaches the front end of the shoe 21 and which has flexibility. This prevents the tread plate member 23 from being displaced.

Here, the tread plate member 23 could be formed of a single rigid plate which extends from the heel to the toe of the foot F. This, however, would limit the freedom of the motions of user's toes, especially the dorsiflexion of toes. As a solution thereto, using the flexible extension plate 23a of the tread plate member 23, as in the present embodiment, is advantageous in securing the freedom of toe motions. If a portion of the extension plate 23a which is positioned within the range of about 15 mm to the front and to the back from immediately below the MP joint Fa has flexibility, then the freedom of toe motions can be secured. Hence, the portion of the extension plate 23a which is positioned at farther front than the aforesaid portion may be formed of a rigid plate.

Meanwhile, securing the foot motion freedom of the user by cantilevering the connecting member 22 sometimes causes a habitual walking pattern of each user to develop a marked influence, resulting in major load being applied to the lateral outer side of a foot or major load being applied to the lateral inner side thereof. For this reason, as illustrated in FIG. 3(b), the tread force sensor 5 of #1 positioned in one location adjacent to the heel of the foot, and the tread force sensors 5 and 5 of #2 and #3, positioned in two locations, which are spaced apart in the lateral direction and which are adjacent to the toe, are installed on the sole 21a. To be more specifically, the tread force sensor 5 of #2 is positioned in the vicinity of the MP joint of the big toe, while the tread force sensor 5 of #3 is positioned in the vicinity of the MP joint of the fourth toe. The tread force sensors 5 and 5 of #2 and #3 are preferably installed such that they will not be displaced toward the heel by 30 mm or more from immediately below the MP joints in order to prevent interference with the dorsiflex of the toes while walking.

Installing the tread force sensors 5 as described above permits accurate detection of a tread force by the tread force sensor 5 of #3 and the tread force sensor 5 of #1 in the case where major load is applied to the lateral outer side of the foot. Further, in the case where major load is applied to the lateral inner side of the foot, the tread force can be accurately detected by the tread force sensor 5 of #2 and the tread force sensor 5 of #1. Hence, even if the influence of the habitual walking pattern of each user markedly manifests, tread forces can be accurately detected by securing the freedom of the foot motions of a user. As a result, the control of the body weight support assisting force based on the tread force of each foot can be reliably accomplished.

Further, the direction in which a tread force is applied varies while walking. Using a multi-axis force sensor as the tread force sensor 5 permits the detection of tread forces in directions besides the vertical direction. This, however, would make the tread force sensor 5 larger, making it difficult to install in a limited place in the shoe 21.

Therefore, according to the present embodiment, each of the tread force sensors 5 is constituted of a base plate 51, a load detector 52 formed of a one-axis strain sensor provided on the base plate 51, a dome-shaped elastic member 53, which covers the load detector 52 and which is made of a resin or the like, and an upper plate 54 placed on the elastic member 53, as illustrated in FIG. 4. The base plate 51 and the upper plate 54 are constituted of rigid plates of stainless steel or the like which is sufficiently rigid to restrain significant deformation when the weight of a user acts thereon. Further, the upper plate 54 is semi-fixed by an elastic gel 55 so as to secure the freedom of motions which permits a posture orthogonal to the direction in which a force is applied. Incidentally, the upper plate 54 may alternatively be semi-fixed by taping.

A tread force is input to the upper plate 54 of the tread force sensor 5 through the intermediary of the insole 21b from a foot of a user. Even if the tread force is input to the upper plate 54 from a direction which is aslant relative to the vertical direction of the load detector 52, an internal stress of the elastic member 53 ensures efficient transfer of the tread force from the vertical direction to the load detector 52. Thus, the improved sensitivity to tread forces in directions besides the vertical direction allows tread force detection failures to be reduced. Moreover, the tread force sensors 5 can be made smaller than a multi-axis force sensor, enabling the tread force sensors 5 to be reasonably installed in the limited place in the shoe 21.

Further, in the present embodiment, the tread plate member 23 is provided with a relief hole 23b for each of the tread force sensors 5, as illustrated in FIG. 3(b). This prevents the upper plate 54 of each of the tread force sensors 5 from interfering with the tread plate member 23. Hence, a force transferred from the leg link 3 to the tread plate member 23 through the intermediary of the connecting member 22 is not input to the tread force sensor 5. As a result, a tread force of the user can be accurately detected without being influenced by a body weight support assisting force to be generated at the leg link 3.

The above has described the embodiment of the present invention with reference to the accompanying drawings; however, the present invention is not limited thereto. For example, in the aforesaid embodiment, the tread force sensors 5 have been installed in a total of three locations, namely, in one location adjacent to the heel of a foot and in two locations adjacent to the toes thereof. Alternatively, however, it is possible to install the tread force sensors 5 in two or more locations adjacent to the heel or in three or more locations adjacent to the toes and laterally spaced apart from each other. Further, one distributed pressure sensor, which is long in the lateral direction, may be installed adjacently to the toes. In this case, a tread force can be detected by the distributed pressure sensor in a plurality of locations in the lateral direction and adjacent to the toes. Even if the number of the distributed pressure sensors is one, tread force sensors will be installed virtually in a plurality of locations in the lateral direction and adjacent to the toes. Similarly, a distributed pressure sensor may be used as the tread force sensor adjacent to the heel.

Further, in the aforesaid embodiment, the sole 21a has been described as the ground contact member of the foot-worn assembly 2; however, the ground contact member means a portion having a function for transmitting load from a user to a ground surface, and a member like the insole 21b, which does not directly come in contact with the ground surface, is also included in the ground contact member. In addition, the tread force sensors 5 may alternatively be installed on the insole 21b. Further, in the aforesaid embodiment, the connecting member 22 rises from the lateral inner side of the sole 21a; alternatively however, the connecting member may rise in the cantilever manner from the lateral outer side of the sole 21a.

Further, in the aforesaid embodiment, the leg link 3 is comprised of the bendable link having the rotary second joint 33 at the middle thereof. Alternatively, however, the leg link may be comprised of a stretchable link having a linear-motion second joint. Further, the load transmitting assembly may be constituted of a harness to be worn around the waist of a user. In addition, to assist the walking of a user having a problem with one leg due to bone fracture or the like, only one of the right and the left leg links 3 and 3 in the embodiment, whichever leg the user is having a problem with, may be used and the other leg link may be omitted.

BRIEF DESCRIPTION OF THE DRAWINGS

FIG. 3(b) is a plan view of the foot-worn assembly of the embodiment with a part thereof omitted.

DESCRIPTION OF REFERENCE NUMERALS

Figure 1:
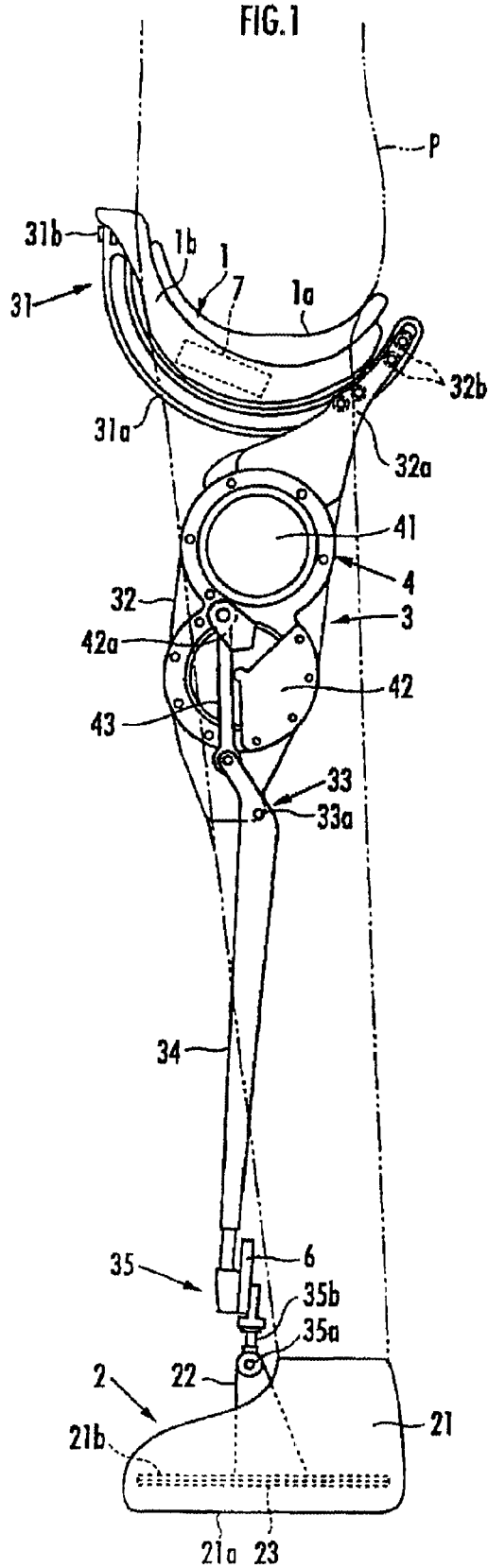
FIG. 1 is a side view of an embodiment of a walking assistance device in accordance with the present invention.
Figure 2:
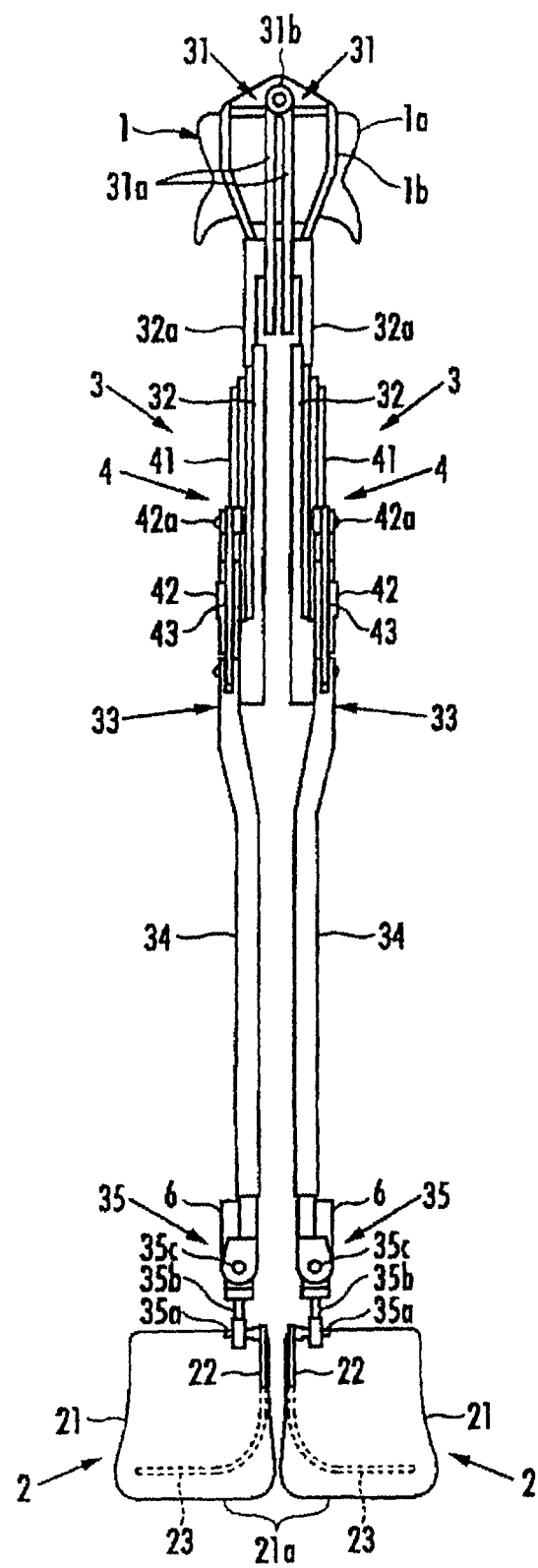
FIG. 2 is a front view of the embodiment.
Figure 3:
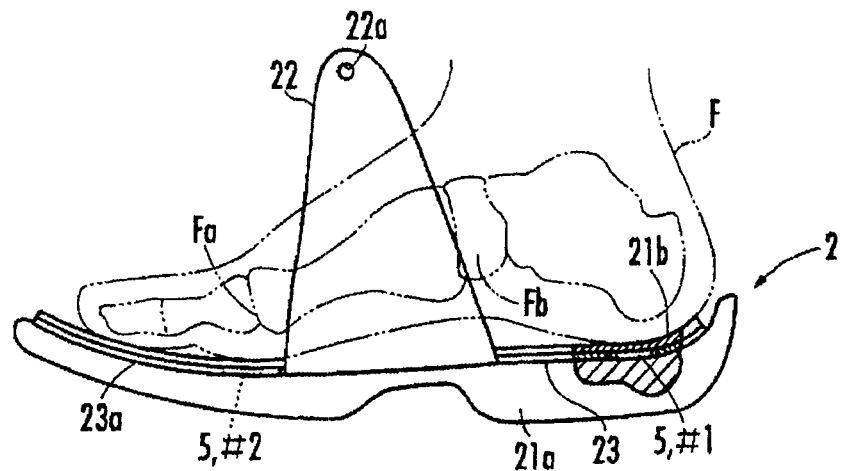
FIG. 3 (a) is a side view of a foot-worn assembly of the embodiment with a part thereof omitted.
Figure 3:
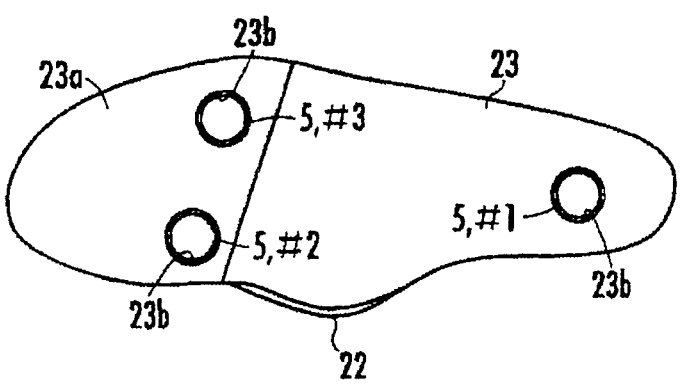
Figure 4:
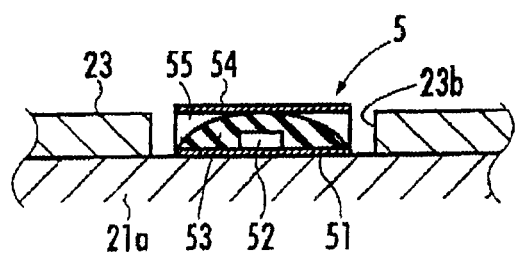
FIG. 4 is a sectional view of a tread force sensor installed on the foot-worn assembly of the embodiment.

1 . . . Seating member (Load transmitting assembly), 2 . . . Foot-worn assembly, 21 . . . Shoe, 21a . . . Sole (Ground contact member), 22 . . . Connecting member, 23 . . . Tread plate, 3 . . . Leg link, 35 . . . Third joint . . . (Joint at the lower end of a leg link), 5 . . . Tread force sensor, 51 . . . Base plate, 52 . . . Load detector, 53 . . . Elastic member, 54 . . . Upper plate

The invention claimed is:

1. A walking assistance device, comprising: a load transmitting assembly, a foot-worn assembly to be attached to a foot of a user, and a leg link provided between the load transmitting assembly and the foot-worn assembly, so as to support at least a part of the weight of the user by the leg link through the intermediary of the load transmitting assembly, the foot-worn assembly including a ground contact member, on which a foot of the user is rested, and a connecting member which connects the ground contact member to a joint provided at a lower end of the leg link, and the ground contact member being provided with tread force sensors for detecting a tread force of the user,
 wherein the connecting member is formed so as to rise in a cantilever manner from one lateral side of the ground contact member, and
 the tread force sensors are installed in at least one location adjacent to the heel of a foot of the user and in at least two locations adjacent to a toe, the two locations being laterally spaced apart from each other.

2. The walking assistance device according to claim 1, wherein the tread force sensor comprises a base plate, a load detector which is provided on the base plate to detect load, an elastic member covering the load detector, and an upper plate composed of a rigid plate rested on the elastic member.

3. The walking assistance device according to claim 2, wherein a tread plate member, which is connected to a lower end of the connecting member and on which a foot of the user steps, is laid on the ground contact member, and the tread force sensor is installed such that the upper plate does not interfere with the tread plate member.

* * * * *